United States Patent [19]

Barsoum

[11] Patent Number: 4,956,288

[45] Date of Patent: Sep. 11, 1990

[54] METHOD FOR PRODUCING CELLS CONTAINING STABLY INTEGRATED FOREIGN DNA AT A HIGH COPY NUMBER, THE CELLS PRODUCED BY THIS METHOD, AND THE USE OF THESE CELLS TO PRODUCE THE POLYPEPTIDES CODED FOR BY THE FOREIGN DNA

[75] Inventor: James G. Barsoum, Quincy, Mass.

[73] Assignee: Biogen, Inc., Cambridge, Mass.

[21] Appl. No.: 185,212

[22] Filed: Apr. 22, 1988

[51] Int. Cl.[5] .................. C12N 15/00; C12N 1/20; C12P 21/00

[52] U.S. Cl. .................. 435/172.3; 435/172.1; 435/252.3; 435/69.1; 435/70.1; 435/71.1; 935/16; 935/33; 935/52

[58] Field of Search .............. 435/172.1, 172.3, 252.3, 435/69.1, 70.1, 71.1; 935/16, 33, 52, 66

[56] References Cited

U.S. PATENT DOCUMENTS

| | | | |
|---|---|---|---|
| 4,740,461 | 4/1988 | Kaufman | 435/68 |
| 4,910,140 | 3/1990 | Dower | 435/173 |

OTHER PUBLICATIONS

Christou et al. (1987), PNAS 84: 3962-3966.
Riggs et al. (1986), PNAS 83: 5602-5606.
S. S. Boggs, R. G. Gregg, N. Borenstein, and O. Smithies, "Efficient Transformation and Frequent Single-Site, Single-Copy Insertion of DNA can be Obtained in Mouse Erythroleukemia Cells Transformed by Electroporation", *Exp. Hematol.*, 14, pp. 988-994 (1986), [Boggs et al.].
G. Chu, H. Hayakawa, and P. Berg, "Electroporation for the Efficient Transfection of Mammalian Cells with DNA", *Nucl. Acids Res.*, 15, pp. 1311-1326 (1987), [Chu et al.].
F. G. Falkner, E. Neumann, and H. G. Zachau, "Tissue Specificity of the Initiation of Immunoglobulin k Gene Transcription", *Hoppe-Seyler's Z. Physiol. Chem.*, 365, pp. 1331-1343 (1984), [Falkner et al.].
M. R. Johnson, C. Norman, M. A. Reeve, J. Scully, and N. J. Proudfoot, "Tripartite Sequences Within and 3' to the Sea Urchin H2A Histone Gene Display Properties Associated with a Transcriptional Termination Process", *Mol. Cell. Biol.*, 6, pp. 4008-4018 (1986), [Johnson et al.].
R. J. Kaufman and P. A. Sharp, "Amplification and Expression of Sequences Cotransfected with a Modular Dihydrofolate Reductase Complementary DNA Gene", *J. Mol. Biol.*, 159, pp. 601-621 (1982), [Kaufman and Sharp].
R. J. Kaufman, L. C. Wasley, A. J. Spiliotes, S. D. Gossels, S. A. Latt, G. R. Larsen, and R. M. Kay, "Coamplification and Coexpression of Human Tissue-Type Plasminogen Activator and Murine Dihydrofolate Reductase Sequences in Chinese Hamster Ovary Cells", *Mol. Cell. Biol.*, 5, pp. 1750-1759 (1985), [Kaufman et al.].
J. C. Knutson and D. Yee, "Electroporation Parameters Affecting Transfer of DNA into Mammalian Cells", *Anal. Biochem.*, 164, pp. 44-52 (1987), [Knutson and Yee].
T. H. Manoharan, R. B. Puchalski, J. A. Burgess, C. B. Pickett, and W. E. Fahl, "Promoter-Glutathione S-Transferase Ya cDNA Hybrid Genes", *J. Biol. Chem.*, 262, pp. 3739-3745 (1987), [Manoharan et al.].
E. Neumann, "Electric Gene Transfer into Culture Cells", *Bioelectrochem. Bioenergetics*, 13, pp. 219-223 (1984), [Neuman].
E. Neumann and P. Bierth, "Gene Transfer by Electroporation", *Am. Biotechnol. Lab*, pp. 10-15, Mar.-/Apr. 1986, [Neuman and Bierth].

(List continued on next page.)

Primary Examiner—Richard A. Schwartz
Assistant Examiner—Anne Brown
Attorney, Agent, or Firm—James F. Haley, Jr.; Emily A. Evans

[57] ABSTRACT

An improved method, employing electroporation, for producing novel recombinant host cells characterized by stably integrated foreign DNA at high copy number. These recombinant host cells are useful in the efficient, large-scale production of recombinant proteins and polypeptides.

20 Claims, 3 Drawing Sheets

OTHER PUBLICATIONS

H. Potter, L. Weir, and P. Leder, "Enhancer-Dependent Expression of Human k Immunoglobulin Genes Introduced into Mouse Pre-B Lymphocytes by Electroporation", *Proc. Natl. Acad. Sci. U.S.A.*, 81, pp. 7161-7165 (1984), [Potter et al.].

M. Reiss, M. M. Jastreboff, J. R. Bertino, and R. Narayanan, "DNA-Mediated Gene Transfer into Epidermal Cells Using Electroporation", *Biochem. Biophys. Res. Commun.*, 137, pp. 244-249 (1986), [Reiss et al.].

G. Ringold, B. Dieckmann, and F. Lee, "Co-Expression and Amplification of Dihydrofolate Reductase cDNA and the *Escherichia coli* XGPRT Gene in Chinese Hamster Ovary Cells", *J. Mol. Appl. Genet.*, 1, pp. 165-175 (1981) [Ringold et al.].

J. M. Roberts, L. B. Buck, and R. Axel, "A Structure for Amplified DNA", *Cell*, 33, pp. 53-63 (1983), [Roberts et al.].

K. Sato, R. Ito, K. H. Baek, and K. Agarwal, "A Specific DNA Sequence Controls Termination of Transcription in the Gastrin Gene", *Mol. Cell. Biol.*, 6, pp. 1032-1043 (1986) [Sato et al.].

R. T. Schimke, "Gene Amplification in Cultured Animal Cells", *Cell*, 37, pp. 705-713 (1984) [Schimke].

M. Wigler, M. Perucho, D. Kurtz, S. Dana, A. Pellicer, R. Axel, and S. Silverstein, "Transformation of Mammalian Cells with an Amplifiable Dominant-Acting Gene", *Proc. Natl. Acad. Sci. U.S.A.*, 77, pp. 3567-3570 (1980) [Wigler et al.].

D. Zerbib, F. Amalric, and J. Tiessie, "Electric Field Mediated Transformation: Isolation and Characterization of a tk Subclone", *Biochem. Biophys. Res. Commun.*, 129, pp. 611-618 (1985) [Zerbib et al.].

FIG. 2 (con't)
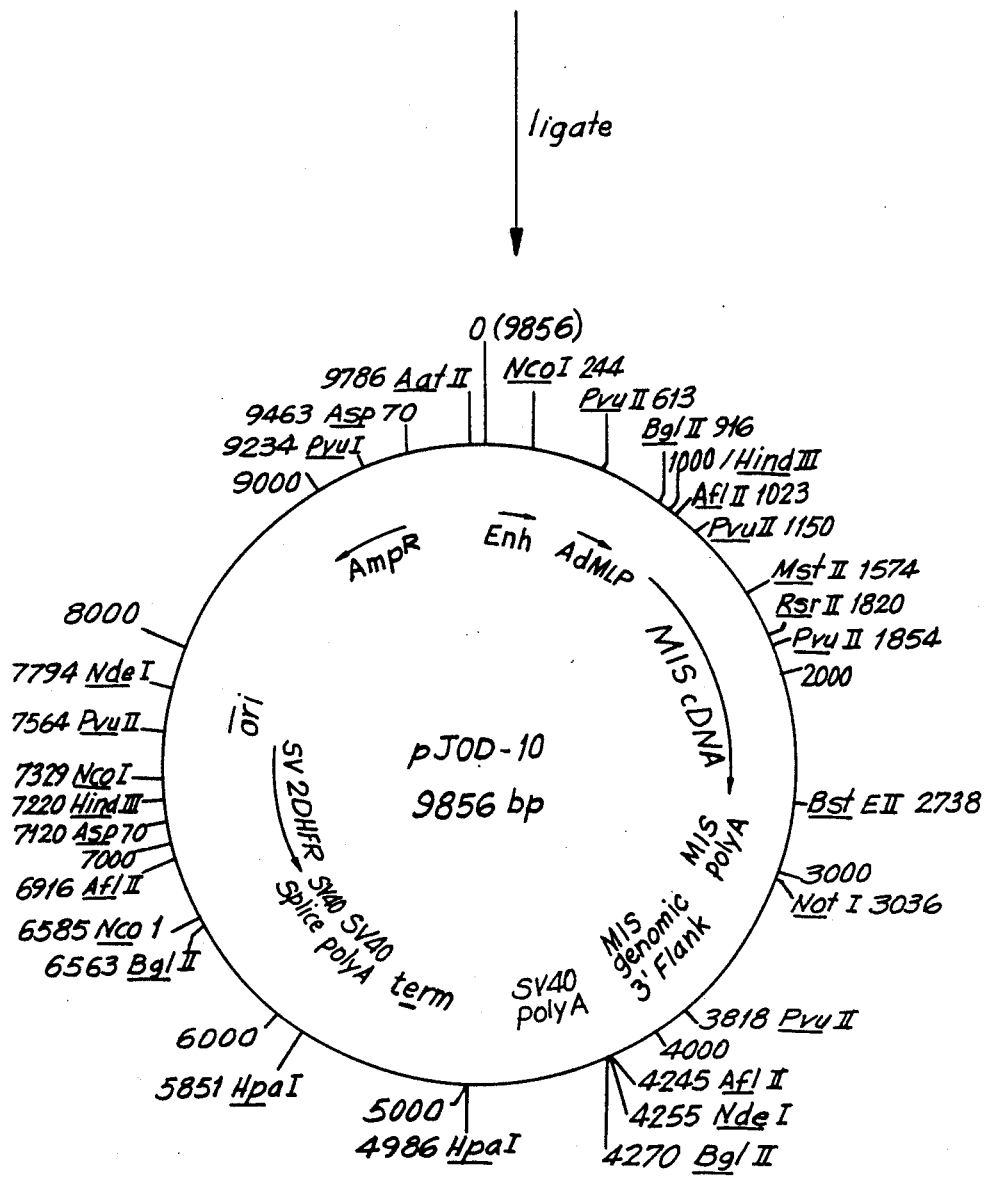

METHOD FOR PRODUCING CELLS CONTAINING STABLY INTEGRATED FOREIGN DNA AT A HIGH COPY NUMBER, THE CELLS PRODUCED BY THIS METHOD, AND THE USE OF THESE CELLS TO PRODUCE THE POLYPEPTIDES CODED FOR BY THE FOREIGN DNA

TECHNICAL FIELD OF THE INVENTION

This invention relates to an improved method, employing electroporation, for producing novel recombinant host cells characterized by stably integrated foreign DNA at high copy number. These recombinant host cells are useful in the efficient, large-scale production of recombinant proteins and polypeptides.

BACKGROUND OF THE INVENTION

The isolation of commercially useful quantities of polypeptides from their natural biological sources is often difficult and expensive. This difficulty is usually due to either a scarcity of source material or the presence of small amounts of polypeptide per unit of source material. Commonly, both of these factors operate simultaneously.

Advances in biotechnology have eased the production and isolation of polypeptides and proteins. A DNA sequence coding for a desired polypeptide or protein may be inserted into a cloning vector along with appropriate regulatory sequences. The introduction of such a vector into a compatible host cell will result in production by the host cell of the polypeptide encoded by the inserted DNA sequence. Because of the cost of culturing cells and isolating the desired proteins from the cultures, the biotechnology industry has long sought methods to increase the yield of protein product produced per unit volume of transformed cell culture as well as the yield per unit time.

The level of production of a product by recombinant host cells is controlled by three major factors: (i) the number of copies of a DNA sequence coding for the product ("copy number") in the cell; (ii) the efficiency with which this DNA sequence is transcribed into messenger RNA; and (iii) the efficiency with which this messenger RNA is translated to generate the protein product. Efficiency of transcription and translation (which together comprise expression) is in turn dependent upon regulatory sequences located upstream and downstream of, and in some instances internal to, the product gene.

None of the methods known in the art for introducing foreign DNA into eukaryotic cells results in stable integration of greater than approximately twenty copies of this foreign DNA into the host cell genome. Instead, these low copy number integrants must be treated to amplify their integrated foreign DNA, in order to produce high copy number integrants. The most widely used procedure to obtain high copy number integrants utilizes the dihydrofolate reductase ("DHFR") gene.

Mammalian cells which contain multiple copies of the DHFR gene are selected when a culture of these cells is subjected to sequentially increasing concentrations of methotrexate (Alt et al., "Selective Multiplication of Dihydrofolate Reductase Genes in Methotrexate-Resistant Variants of Cultured Murine Cells", *J. Biol. Chem.*, 253, pp. 1357-79 (1978)). DHFR is an essential enzyme for cell survival. Since methotrexate ("MTX") is a competitive inhibitor of DHRF, only those cells that have increased their DHFR content (e.g. by amplifying the resident DHRF gene) to offset MTX inhibition will survive. Furthermore, as the MTX concentration is sequentially increased, cells will require increasing amounts of DHFR, and thus higher DHFR gene copy numbers, to survive. This is the basis of the DHFR gene amplification procedure.

One indication that the DHFR gene might be useful in the amplification of the cotransfected genes was the report that when *Escherichia coli* plasmid pBR322 was cotransfected (introduced together) with genomic DNA containing a MTX-resistant DHFR gene into mouse cells, the pBR322 DNA was also amplified by MTX selection (Wigler et al., "Transformation of Mammalian Cells with an Amplifiable Dominant-Acting Gene", *Proc. Natl. Acad. Sci. USA*, 77(6), pp. 3567-70 (1980)). However, most of the Wigler transfectants did not amplify the pBR322 DNA more than several-fold.

The generation of very high copy number integrants was made possible by the isolation of Chinese hamster cells deficient in native DHFR activity ("DHFR−CHO cells") (Urlaub and Chasin, "Isolation of Chinese Hamster Cell Mutants Deficient in Dihydrofolate Reductase Activity", *Proc. Natl. Acad. Sci. USA*, 77(7), 4216-20 (1980). Transfection of these DHFR−CHO cells with a plasmid containing both the DHFR gene and the *E. coli* gpt gene, followed by MTX selection, produced recombinant host cells which had amplified the gpt gene approximately 50-fold (Ringold et al., "Co-expression and Amplification of Dihydrofolate Reductase cDNA and the *Escherichia coli* XGPRT gene in Chinese Hamster Ovary Cells", *J. Mol. Appl. Genet.*, 1, pp. 165-75 (1981)).

In a more dramatic example of the possibility for amplification of non-selectable genes using this technique, transfection of DHFR−CHO cells with plasmids containing both the murine DHFR gene and the SV40 early region, followed by sequential step-wise increases in the MTX concentration of the growth medium, produced cells containing up to 1000 copies of the transforming DNA (Kaufman and Sharp, "Amplification and Expression of Sequences Cotransfected with a Modular Dihydrofolate Reductase Complementary DNA Gene", *J. Mol. Biol.*, 159, pp. 601-21 (1982)).

While the DHFR/MTX amplification procedure produces cells with amplified copies of transfected DNA, it has several serious drawbacks. These drawbacks include the slowness of the procedure, the necessity of using DHFR−cells to obtain significant amplification, and the fluidity of amplified DNA.

To select recombinant host cells which have amplified transfected DNA to a very high copy number, they must be subjected to sequential step-wise increases in the MTX concentration of the growth medium. This is a lengthy process. In our hands, six to ten months are required to achieve a several hundred-fold amplification. Obviously, a more expeditious procedure would be desirable.

Another drawback of the DHFR/MTX amplification procedure is that it does not work well for cells that contain a DHFR gene ("DHFR+cells"). At best, only a fifty-fold amplification of transfected DNA has been reported in DHFR+cells (Wigler et al., "Transformation of Mammalian Cells with an Amplifiable Dominant-Acting Gene", *Proc. Natl. Acad. Sci. USA*, 77(6), pp. 3567-70 (1980)). The production of DHFR−cells from DHFR+cells, if possible at all for a given cell type, is lengthy and laborious (Urlaub and Chasin, "Isolation of Chinese Hamster Cell Mutants Deficient in Dihydrofolate Reductase Activity", *Proc. Natl. Acad. Sci. USA*, 77(7), pp. 4216-20 (1980)). Since all mammalian cells possess the DHFR gene, a worker looking for significant amplification of transfected DNA would be restricted to using DHFR−CHO cells unless he was willing to face the ordeal of creating a new DHFR−cell type.

An additional drawback of DHFR/MTX amplification is that not all sequences contained within transfected DNA will be amplified to the same degree (Kaufman and Sharp, "Amplification and Expression of Sequences Cotransfected with a Modular Dihydrofolate Reductase Complementary DNA Gene", *J. Mol. Biol.*, 159, pp. 601-21 (19B2)). Of equal concern are reports of deletions and rearrangements within amplified DNA (see, e.g., Kaufman and Sharp, id.; Schimke, "Gene Amplification in Cultured Animal Cells", *Cell*, 37, pp. 705-13 (1984)).

SUMMARY OF THE INVENTION

The present invention relates to a novel recombinant host cells containing stably integrated foreign DNA which is at a high copy number. The present invention also includes the novel cells produced by the process of this invention.

A process of the present invention, as illustrated by one embodiment, is set forth below. An initial population of cells is transfected with DNA. This DNA comprises a qene coding for a desired polypeptide (the "product qene"). The transfecting DNA also comprises a "protective gene" that, on expression, codes for a protein in an amount capable of protecting the recombinant host cell against a toxic substance, wherein increasingly higher copy numbers of this gene are required to protect the recombinant host cell against increasing concentrations of this toxic substance. Alternatively, the protective gene may code, on expression, for a protein in an amount capable of protecting the recombinant host cell from decreases in the concentration of a previously essential nutritive substance. After electroporation, the cells are cultured for a time sufficient to allow these cells to recover from this transfection process, integrate foreign DNA at high copy number, and establish high level expression of the protective genes. Finally, the cells are subjected to a sufficiently high concentration of the toxic substance, or a sufficiently low concentration of the nutritive substance, that the protective gene was designed to protect against, killing or severely retarding the growth of those cells with a low copy number.

The process of this invention has numerous advantages over prior art methods and generally solves many of the problems associated with these methods.

Accordingly, it is an object of the present invention to provide a process which produces recombinant host cells containing stably integrated foreign DNA at a high copy number within a reasonable period of time. Another object of the present invention is that this process may successfully be applied to any eukaryotic cell. Yet another object of the present invention is that, in the cells produced by this process, the copy number of the gene coding for a polypeptide of interest wi generally be independent of the particular product gene chosen.

A still further object of this invention is to provide novel recombinant host cells with very high expression levels of desired gene products.

These and other additional objects and advantages of the present invention are apparent from the detailed description and claims which follow.

In a preferred embodiment of the present invention, an initial population of cells is subjected to electroporation in the presence of foreign DNA. The foreign DNA comprises: (i) at least one protective gene coding for a protein capable of protecting the recombinant host cells against a toxic substance, wherein inCreasingly higher copy numbers of the protective gene are required for, and capable of protecting the recombinant host cell against increasing concentrations of the toxic substance; (ii) at east one product gene coding for a polypeptide whose production is desired; and (iii) at least one selective gene coding for a protein, wherein the presence of one copy per cell of the selective gene is sufficient to protect the recombinant host cell against either decreases in the concentration of a nutritive substance or the presence of a toxic substance. These genes are operably linked to regulatory sequences that are compatible with the recombinant host cells.

Following electroporation, the cells are cultured for a time sufficient to allow them to recover from the electroporation process. After recovery, the cells are exposed to either: (i) a toxic substance against which the product of the selective gene provides protection, at a concentration sufficiently high to kill or severely retard the division of those cells which did not incorporate at least one copy of the foreign DNA in the electroporation process or (ii) a decreased amount of a nutritive substance which the product of the selective gene makes non-essential in the context of the selection scheme, for a time sufficient to kill or severely retard the division of those cells that did not incorporate at least one copy of the foreign DNA into their qenomes after electroporation.

Finally, the cells are exposed to a sufficiently high concentration of the toxic substance, or a sufficiently low concentration of the nutritive substance which the protective gene protects against, killing or severely retarding the division of those cells with a low copy number.

DETAILED DESCRIPTION OF THE INVENTION

Figure 1:
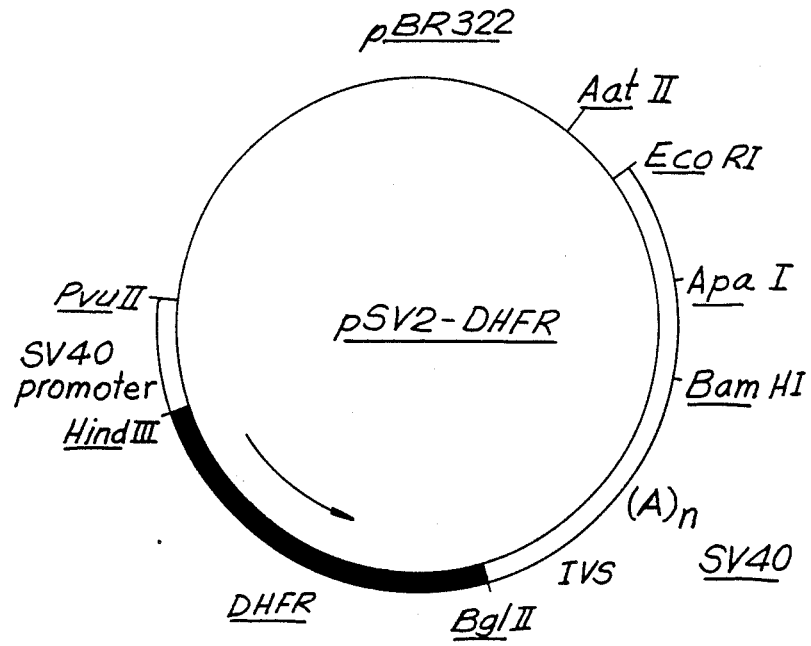
FIG. 1 is a pictorial representation of vector pSV2-DHFR

The present invention relates to a novel process, employing electroporation, for preparing recombinant host cells containing stably integrated foreign DNA at a high copy number, as well as to the novel cells produced by this process For the purposes of this application, "high copy number" means at least fifty integrated copies of foreign DNA per recombinant host cell. Preferably, high copy number will be at least 100 copies per cell. Most preferably, high copy number will be 300 to 1000 copies per cell. For the purposes of this application, "low copy number" means less than about fifty copies of foreign DNA per recombinant host cell.

Cells

The recombinant host cells of this invention may be prepared, according to the method of this invention, from any eukaryotic cells. For example, cells of fungal, animal and plant origin would be appropriate. Host cells of animal origin are preferred for the production of polypeptides and proteins for use as pharmaceuticals and as medical diagnostic reagents. Useful animal cells may include B and T lymphocytes, leukocytes, fibroblasts, hepatocytes, pancreatic cells, and undifferentiated cells. Often, immortalized mammalian cell lines would be utilized. By way of example, useful mammalian cell lines would include 3T3 3T6 STO CHO Ltk$^-$, FT02B, Hep3B, AR42J and MPC11. Preferred mammalian cell lines are CHO, 3T3, and Ltk$^-$. While the frequency of stable transformants, and the expression level of transferred genes, will depend on the particular cell type used, the selection of a particular host is not part of this invention. Rather this invention is applicable generally to the rapid production of recombinant cells containing stably integrated foreign DNA at a high copy number, from any eukaryotic cell

Foreign DNA

The term "foreign DNA", as used in this application, refers to any DNA that is introduced into a host cell. This foreign DNA may be derived from a variety of sources. These sources include genomic DNA, cDNA, synthetic DNA and combinations thereof. If the foreign DNA comprises genomic DNA, it may include naturally occurring introns, located upstream, downstream, or internal to any included genes. Foreign DNA may also include DNA derived from the same cell line or cell type as the host cell, as well as DNA which is homologous or complementary to DNA of the host cell.

The foreign DNA will include at least one gene coding for a polypeptide or protein whose production is desired ("product gene") and at least one "protective gene", as defined infra Preferably, the foreign DNA will also include at least one "selective gene", as defined infra These genes may be contained in the foreign DNA within a single DNA molecule, within separate DNA molecules, or within combinations thereof.

The process of this invention is applicable to a wide variety of product genes and will result in cells with a high copy number of the desired product gene. This high copy number will usually result in high expression levels of the desired gene product. For example, products such as cellular receptors, the active components of vaccines or other pharmaceutically active products agriculturally or other commercially useful compositions, enzymes, antibiotics, food stuffs and the like are usefully produced by the recombinant host cells produced by the process of this invention. Some specific examples of desirable product genes are those coding for tissue plasminogen activator, Müllerian inhibiting substance, factor VIII, erythropoietin and soluble CD4. Again, the selection of a particular product gene is not a part of this invention. Rather this invention is generally applicable to producing recombinant host cells with high expression levels of desired gene products due to the high copy number of product genes in the recombinant host cell.

As used in this application, a "protective gene" is a gene that, on expression, is capable of protecting the recombinant host cell from a toxic substance, where increasingly higher copy numbers of this protective gene are required to protect the recombinant host cell against increasing concentrations of the toxic substance. Alternatively, the protective gene may code for a protein that is capable of protecting the recombinant cell from decreases in the concentration of a previously essential nutritive substance in the culture medium, where increasingly higher copy numbers of the protective gene are required to protect the recombinant host cell against decreasing concentrations of the nutritive substance.

In general, any gene that is amplified when the host cell containing it is subjected to suitable selection pressure will serve as a protective gene for the purposes of the present invention Thus, a great variety of protective genes may be utilized, providing that, at the level they are expressed, their gene products are capable of protecting the host cell from a toxic substance or the lack of a nutritive substance, and, providing that the degree of protection these gene products confer is roughly proportional to the copy number of the protective gene. For example, if the product of a protective gene protects the cell from a toxic substance, then increasingly higher copy numbers of this gene are required to protect the recombinant host cell from increasing concentrations of the toxic substance that the protective gene was designed to protect against In the context of this application, "protection" of the recombinant host cells means that cell division is not severely inhibited. A failure of protection would thus indicate either the death of the cells or a severe inhibition of cell division. There are three broad classes of protective genes.

The first class of protective genes includes those genes that confer the desired protection on their host cell (i.e., allow for selection of cells comprising high copy number foreign DNA) even when expressed from efficient promoters. Examples of this type of protective gene and the toxic substances these genes protect against include: dihydrofolate reductase (methotrexate), metallothionein (heavy metals, e g., cadmium), CAD (N-(phosphonacetyl)-L-aspartate), 3-hydroxy-3-methylglutaryl coenzyme A reductase (compactin), adenosine deaminase (deoxycoformycin-alanosine-adenosine-uridine), uridine monophosphate synthetase (pyrazofurin), glutamine synthetase (methionine sulfoxine in gutamine-free media), asparagine synthetase ($\beta$-aspartylhydroamate), ribonucleotide reductase (hydroxyurea), thymidilate synthetase (5-fluoro-deoxyuridine , ornithine decarboxylase (difluoromethylornithine), and promoter glutathione S-transferase Ya (benzo($\alpha$)pyrene antidiol epoxide). Examples of this type of protective gene and the nutritive substances whose reduction or absence they protect against include: thymidine kinase (thymidine) and xanthine-guanine phosphoribosyl transferase (xanthine).

The second class of protective genes includes those dominant selectable marker genes that, when expressed from efficient promoters, confer the desired protection on their host cell (i.e., allow for selection of cells comprising high copy number foreign DNA) by virtue of point or deletion mutations that greatly impair the ability of their gene products to protect the host cell from selection pressure. Thus, a typical selective gene, whose gene product at normal expression levels is so active that the host cell requires only one gene copy to survive a wide range of selection pressure, may be "converted" to a protective gene. Such a "conversion" would be accomplished by mutating the selective gene so that the ability of its gene product to protect the host cell from selection pressure is substantially impaired. The host cell of such a mutated gene would then require increasingly higher copy numbers of this mutated gene to survive increasingly stringent selection pressure.

The third class of protective genes includes those selective genes that confer the desired protection on the host cell by virtue of the fact that they are expressed at extremely low levels. This low expression level may be achieved either by drastically reducing translation or transcription. One way to effectively reduce translation would be to situate the selective gene so that it constitutes the second coding region of a dicistronic messenger RNA. To effectively inhibit transcription of the selective gene, it may be coupled to a profoundly defective, or inoperable, promoter Alternatively, all but the TATA box of the promoter may be deleted. By severely inhibiting expression of the selective gene, it is, in effect, being functionally converted to a protective gene, so that a single copy of this gene is no longer sufficient to protect the host cell over a wide range of selection pressure. Rather, increasingly higher copy numbers of this gene are required to protect the host cell from increasingly stringent selection pressure.

In a preferred embodiment of this invention, the foreign DNA will also include at east one "selective gene". As used in this application, a "selective gene" is a gene (dominant selectable marker) coding for a protein that is capable of protecting the recombinant host cell from either the presence of a toxic substance or the absence of a nutritive substance, where the presence of only one copy of the selective gene is sufficient to protect the recombinant host cell over a wide range of selection pressure. Examples of useful selective genes include: neo (G418 resistance), qpt (xanthine utilization in the presence of mycophenolic acid), hisD (histidinol utilization, and hygro (hygromycin B resistance).

Except for the third class of protective genes noted above, each protective, selective and product gene must be operably linked to a 5'-noncoding DNA sequence comprising transcriptional and translational initiation elements which are compatible with the particular host cell utilized. If two or more genes share the same promoter/enhancer elements (resulting in a multicistronic mRNA), the product gene should be closest to the promoter in order to optimize its expression level. However, it is preferable to link each gene to its own regulatory region. In general, 5'-regulatory sequences will be chosen to maximize expression of the transferred genes, especially product genes.

A wide variety of transcriptional and translational 5'-regulatory sequences may be successfully employed, The transcriptional regulatory sequences must include promoter elements and may include enhancer elements The various 5'-regulatory elements may be derived from one source, or a combination of sources. If a gene is supplied as genomic DNA, the regulatory sequences normally associated with that gene may be utilized. Alternatively, these regulatory elements may be derived from the 5'-noncoding region of other genes. For example, if a mammalian host cell is utilized, these 5'-regulatory elements may be derived from viruses such as adenovirus, bovine papilloma virus, Simian virus 40, cytomegalovirus, or the like, where these sequences are associated with a gene that has a high level of expression. Alternatively, the 5'-noncoding regions of eukaryotic qenes, such as β-actin, with high levels of expression may be used.

It may be advantageous to utilize transcriptional initiation regulatory sequences which allow for repression and activation, so that expression of a particular gene may be modulated at will. Although it will normally be desirable to optimize expression of the transferred genes through the choice of particular 5'-regulatory sequences, so long as the transferred genes are expressed, the choice of 5'-regulatory sequences is not critical. Appropriate 5'-regulatory sequences for a particular host cell may conveniently be chosen from among the available 5'-regulatory sequences that are known in the art to be compatible with that cell type.

Normally, there are 3'-regulatory sequences operably linked to the transferred genes. For example, a poly A addition site is usually positioned downstream of every transferred gene. If the gene is supplied as genomic DNA from a eukaryotic source, the poly A site naturally associated with that gene may be used. Alternatively, the poly A addition sequence of another gene may be employed. This sequence may be contiguous with the transferred gene. Alternatively, the poly A site may be placed further downstream of the gene, either with or without a splice junction.

In a preferred embodiment of this invention, at least one eukaryotic transcriptional terminator element will be positioned downstream of every protective, selective, and product gene. If a gene has an associated poly A addition site, then the terminator element will be positioned downstream of this poly A addition site. The use of such transcriptional terminator elements resulted in an approximately fourfold increase in expression of the product gene.

While not wishing to be bound by theory, we believe that the presence of terminator elements downstream of these genes results in improved expression levels by decreasing transcriptional interference between the genes.

If the foreign DNA consists of plasmid DNA and more than one gene is on each plasmid, then the promoter region of each gene will likely not be very far away from the end of an adjacent gene. Therefore, an RNA polymerase molecule transcribing a gene may continue to progress along the DNA strand past the end of that qene and into the promoter region of the next gene, interfering with the transcription of this downstream gene. If, however, a transcriptional terminator element is positioned between the two genes, the RNA polymerase will not reach the promoter of the downstream gene and will thus not interfere with its tranScription. Accordingly, it is especially preferred that a transcriptional terminator element be placed upstream of any product gene to maximize its expression. However, it is not essential that every selective or protective gene be preceded by a terminator element.

Examples of useful eukaryotic transcriptional terminator elements include the human gastrin gene terminator (Sato et al., "A Specific DNA Sequence Controls Termination of Transcription in the Gastrin Gene", *Mol. Cell. Biol.*, 6, pp. 1032-43 (1986)) and the sea urchin H2A histone gene termination sequence (Johnson et al., "Tripartite Sequences within and 3' to the Sea Urchin H2A Histone Gene Display Properties Associated with a Transcriptional Termination Process", *Mol. Cell. Biol.*, 6, pp. 4008-18 (1986)). However, this invention should not be construed as being limited to these terminator elements. Rather, any sequence which becomes known in the art as having the ability to halt the progression of RNA polymerase II would be appropriate for the purposes of this invention. Preferably, any terminator element used will be positioned in its natural orientation with respect to the gene whose transcription it is to terminate.

In addition to the regulatory elements discussed above, other transcriptional and translational control elements located either within or without the transcribed regions of the genes may be utilized to good advantage. In addition, sequences which increase the frequency of chromosomal integration or recombination and sequences which contain origins of replication may be useful. Among elements located within the transcribed regions of the genes, sequences which enhance RNS processing and export from the nucleus as well as those which stabilize the mRNA and increase its translation may be useful.

The physical state of the foreign DNA is important to its efficient integration into the host cell genome at a high copy number. In the preferred embodiment of this invention, the input foreign DNA will be linear. Supercoiled or relaxed circular DNA is much less preferred. In addition, to practice the preferred embodiment of this invention, the linear input foreign DNA will have compatible cohesive ends results in a 5- to 20-fold greater yield of high copy number integrants than the use of linear DNA with blunt ends. Cohesive ends (also called "sticky ends" in the art) are created by digesting the foreign DNA with a restriction enzyme that makes a staggered cut, resulting in linear DNA in which one strand "overhangs" the other. While we prefer an overhang of at least four base pairs, both longer and shorter overhangs are also useful for the purposes of this invention.

If the input foreign DNA consists of more than one type of DNA molecule (e.g., if the protective gene is on one plasmid and the product gene is on another), each type of DNA molecule should be digested with enzymes that result in linear DNA molecules with cohesive ends that are compatible ("cohesive") with all other DNA molecules in the foreign DNA. While not wishing to be bound by theory, we believe that cohesive ends improve the efficiency of high copy number integration because the foreign DNA molecules may ligate in tandem to form a large DNA molecule and that it is this large DNA molecule that then integrates into the genome. Thus, a single integration event may produce a high copy number integrant.

As stated above, foreign DNA may consist of genomic DNA, synthetic DNA, cDNA or any combination thereof. In the preferred embodiment of this invention, the foreign DNA will consist of plasmid DNA which further comprises sequences allowing for plasmid replication and selection in bacteria. The use of such plasmids iq preferred because they permit convenient production of large quantities of pure foreign DNA. The particular plasmid utilized is not critical to the practice of this invention. Rather, any plasmid known in the art to be capable of being replicated and selected for in bacteria would be a suitable vehicle in which to insert desired product, selective and protective genes, as well as their attendant regulatory sequences.

Each protective, selective and product gene may be contained within a separate DNA molecule. However, in the preferred embodiment of this invention, any product gene will be contained within the same DNA molecule as at least one protective gene. If a selective gene is employed then it is preferable to include this gene on the same DNA molecule as the protective and product genes.

If the foreign DNA consists of DNA molecules that each contain more than one gene, and each of these genes is followed by a transcriptional terminator element, then spacing and orientation of the genes is probably not critical. However, if transcriptional terminator elements are not present, then care ought to be exercised as to the spacing and orientation of the genes within each DNA molecule. A back-to-back orientation of genes is preferred over a head-to tail orientation. If two genes are in a back-to-back orientation, there should be at least 1000 base pairs between their respective poly A sites. If two genes are in a head-to-tail orientation, at least 2000 base pairs should separate the poly A site of the upstream gene from the promoter of the downstream gene.

Electroporation

In order to produce high copy number integrants, the foreign DNA must be introduced into the host cells by electroporation. Preferably, an electroporation protocol which results in efficient DNA transfection (transient introduction of at least about 2000 copies of foreign DNA per cell) would be utilized. In the preferred embodiment of this invention, we use the protocol set forth below. This protocol is a modification of that presented by Chu et al., "Electroporation for the Efficient Transfection of Mammalian Cells with DNA", 15(3), pp. 1311-27 (1987). However, this invention does not exclude alternative electroporation protocols which also result in efficient transfection (i.e., those that result in transient introduction of at least about 2000 copies of foreign DNA per cell).

Preferably, the cells will be fed or passaged on the day prior to electroporation. In addition, at the time the cells are harvested for electroporation, they should be growing exponentially. If monolayer cells are used, they should be one-half confluent. During electroporation, the cell density should be from $5 \times 10^6$ to $3 \times 10^7$ cells/ml. Preferably, the cell density would be $1.25 \times 10^7$ cells/ml.

A high DNA concentration during electroporation will increase the efficiency of transfection. It will also increase the total number of integration events, and the frequency of high copy number integration events. Preferably, the DNA concentration (including carrier DNA) will be 0.5 mg/ml.

The inclusion of carrier DNA results in a significant improvement in the yield of transformants and high copy number integrants. Preferably, the carrier DNA will be approximately 300 to 1000 bp in length. Carrier DNA significantly larger than 1000 bp is toxic to the cells. Sonication may conveniently be used to produce carrier DNA with the desired size distribution. Any genomic DNA would be appropriate for use as carrier. Preferably, salmon sperm DNA would be utilized because of its ready commercial availability in large quantities at reasonable prices. The ratio of foreign DNA to carrier DNA may vary, but the total concentration of DNA is maintained as above. Typically, foreign DNA will comprise 30 to 80% of the total DNA, and preferably 37 to 50%.

The foreign and carrier DNAs are added to the cells and the resulting mixture transferred to the container in which electroporation is to occur. It is not necessary to preincubate cells and DNA prior to electroporation.

We prefer to perform electroporation in a buffer of the following composition: 20 mM Hepes/NaOH, pH 7.05; 137 mM NaCl; 5 mM KCl; 0.7 mM $Na_2HPO_4$; 6 mM dextrose. However, other buffers approximating physiological conditions would be acceptable.

Preferably, electroporation will be carried out at about 25° C. Electroporation at 0-4° C. was five- to twenty-fold less efficient in terms of the yield of primary transformants and high copy number integrants.

A Bio-Rad Gene Pulser TM electroporation apparatus was utilized in the preferred embodiment. However, a different apparatus generating the same waveform would give substantially the same results. The Gene Pulser TM apparatus generates an exponential decay pulse by discharge of a capacitor. The characteristics of the exponential decay waveform will be determined by the following variables: (a) the amount of charge the capacitor will store at a given voltage (usually stated in microfarads), (b) the voltage to which the capacitor is charged, and (c) the resistance of the circuit through which the capacitor is discharged (including the resistance offered by the electroporation buffer by virtue of its volume and ionic strength). Accordingly, it is these variables that must be optimized to achieve the desired results.

Typically, electroporation was performed in 800 $\mu l$ of buffered saline (the exact buffer composition is set forth above). This is the capacity volume of the Gene Pulser TM electroporation cuvette. The capacitor was set to the maximum capacitance that the apparatus would allow (960 $\mu F$). The Gene Pulser TM apparatus will produce a nearly uniform electrical field of strength $E = V/0.4$ cm. The optimal voltage will vary depending upon the cell type; if the voltage is too high, the cells will die. In general, the optimal voltage for a particular cell type will be between about 230-320 V, with the other variables as set forth above. It is a sharp optimum, straying as little as 10 V away from the optimum will result in a significantly lower efficiency of DNA uptake by the cells. A single pulse, lasting approximately 10 milliseconds, is delivered to the contents of the cuvette.

After the pulse, the cells are allowed to stand for a brief rest period (usually 8-10 minutes) before removal from the cuvette. Typically, approximately 20 to 50% of starting cells survive the electroporation process.

Selection

In the preferred embodiment of the present invention, the foreign DNA will include a selective gene, in addition to product and protective genes. In this instance, the cells would be subjected to both a primary, and a secondary selection step. In the primary selection step, cells that have integrated at least one copy of the selective gene are selected. For the primary selection step to work, the selective gene must be expressed. After the secondary selection step, 50-80% of the surviving clones are characterized by high copy number integration of foreign DNA.

Survival at a given selection pressure in secondary selection is not necessarily directly proportional to gene copy number. The location in the host cell genome at which the foreign DNA integrates can have a significant effect on its transcription. Thus, "position effects" will influence the expression level per gene copy. In addition, mutant cells that have an impaired ability to take up the toxic substance, or an improved uptake of the nutritive substance, that the protective gene was designed to protect against, might be able to survive secondary selection without high copy number integration. Finally, it is possible that the protective gene may mutate so that its gene product is resistant to the toxic substance it was designed to protect against. However, these would be rare events. The majority of cells surviving secondary selection are characterized by high copy number integrated foreign DNA.

The timing of the selection steps is important to their success and is set forth below. After the cells are removed from the electroporation cuvette, they are seeded into culture plates in nonselective medium. The cells are cultured in nonselective medium for a time sufficient to allow them to recover from electroporation and express the selective gene. Usually, an incubation of two to four days (or generation times) in non-selective medium is required prior to primary selection. Preferably, an incubation of two days (or generation times) is performed.

Next, the cells are subjected to primary selection by culturing them in medium (i) that is supplemented with the toxic substance that the selective gene was designed to protect against or (ii) that is depleted in the nutritive substance that the selective gene makes non-essential in the context of the selection scheme utilized. The particular toxic or nutritive substance chosen, as well as the appropriate concentration of that substance for primary selection, depends upon which selective gene and selection scheme is utilized, and can be chosen according to standard criteria.

The primary selection step will preferably last four days (generation times). However, primary selection periods of four to six days (or generation times) would be appropriate. The primary selection step either kills or severely retards the division of those cells that are not expressing at least one copy of the selective gene.

The secondary selection step should not be commenced earlier than six days (or generation times) after electroporation, nor later than nine days (or generation times) after electroporation, irrespective of the durations of the non-selective and primary selection incubations. Normally, the secondary selection step would commence seven days (or generation times) after electroporation. While not wishing to be bound by theory, we believe that this lag period is required to allow recovery from electroporation, integration of high copy number foreign DNA and establishment of stable high level expression of the protective genes. In a secondary selection, the cells are cultured in medium (i) that is supplemented with the toxic substance that the protective gene was designed to protect against or (ii) that is depleted in the nutritive substance that the protective gene makes non-essential. The secondary selection step either kills or severely retards the division of those cells that are not expressing large amounts of the protective gene product.

The appropriate concentration of toxic or nutritive substance may be conveniently determined as follows. First, a concentration at which at least 80% of the primary transformants survive should be determined. Next, the cells' resistance to a range of concentrations above that level should be determined, with increases of approximately two-fold between concentrations. This range should include at least one concentration at which no colonies are obtained (survival frequency of less than $10^{-7}$). The appropriate concentration will be that at which the survival frequency is within the range of approximately $5 \times 10^{-6}$ to $1 \times 10^{-7}$.

In an alternative embodiment of the present invention, the foreign DNA will not include a selective gene. In this case, no primary selection step would be performed. After electroporation, the cells are cultured in non-selective medium prior to commencing secondary selection. The appropriate time to commence secondary selection is as described in the previous embodiment.

Once secondary selection has been commenced, the cells must thereafter be cultured in secondary selection medium in order to maintain high copy number. Usually, when colonies large enough to subclone (~1 mm in diameter) have grown up, they are picked and separately expanded. The time required after the commencement of secondary selection until colonies large enough to subclone have grown up depends on the generation time of the particular cell line used and is not critical to practicing the invention. In general, however, clonal cell populations containing foreign DNA at high copy number will be produced by the process of this invention within twenty one days after electroporation.

Alternatively, cells need not be subcloned after secondary selection. If subcloning is not performed, then the resulting cell population would contain cells of varying genotypes. However, the majority of these cells will contain foreign DNA integrated at high copy number.

Recombinant Host Cells

Fifty to eighty percent of the recombinant host cells produced by the process of this invention are characterized by stably integrated high copy number foreign DNA. These cells are novel. Their genomes differ from those of any other cells known in the art.

In cells containing high copy number DNA, produced by traditional gene amplification techniques, the individual repeating units are usually very large, and may range in size from hundreds to thousands of kilobase pairs (see, e.g., Roberts et al., "A Structure for Amplified DNA", *Cell*, 33, pp. 53–63 (1983); Dolnick et al., "Correlation of Dihydrofolate Reductase Elevation with Gene Amplification in a Homogeneously Staining Chromosomal Region in L5178Y Cells", *J. Cell Biol.*, 83, pp. 394–402 (1979)). Individual units contain variable amounts of flanking cellular DNA and/or carrier DNA. Consequently, the repeating units within a particular tandem array are highly heterogeneous in terms of both size and sequence content see, e.g., Roberts et al., id.; Schimke, "Gene Amplification in Cultured Animal Cells", *Cell*, 37, pp. 703–13 (1980)).

In contrast, greater than 70% of the high copy number clones of this invention have foreign DNA copies inserted into the host cell genome in the form of tandem or inverted tandem repeats, with each repeating unit apparently containing only foreign DNA. In these tandem repeat clones, most, but not all of the foreign DNA copies are found in these tandem repeats.

In approximately 80% of these tandem repeat clones, the restriction site used to originally linearize the input foreign DNA was still intact. This result indicates that the occurrence of these high copy number clones is probably due to ligation of the input DNA followed by integration as tandems, rather than by integration of single units followed by gene amplification. Approximately 20% of these clones had tandem repeats in which the original restriction sites had been destroyed by nuclease degradation of 20–200 base pairs at each end.

If all the protective, product and selective genes are contained within the same DNA molecule, then each repeating unit will be essentially identical. When the genes are contained on two or more DNA molecules, then the repeating units will reflect this diversity. If there are different types of foreign DNA repeating units then they will be randomly ligated to form the tandems. In either situation, the orientation of individual units will be random.

In approximately 10–20% of the recombinant host cells, the high copy number foreign DNA is present within the genome as scattered single site single copy, or low copy tandem, insertions.

In approximately 5–10% of the recombinant host cells of this invention, the structure of the integrated copies of foreign DNA was not experimentally discernable.

The copy number of the high copy number clones analyzed was stable for at least 150 generations.

Selection Followed By Amplification

If the recombinant host cells of the previous embodiments are cultured for long periods of time in secondary selection medium, with increasing selection pressure, then at least some of these cells will amplify their complement of foreign DNA by conventional gene amplification. The amplified recombinant host cells so produced would have an even higher foreign DNA copy number than the original high copy number integrants. Presumably, these cells would also have higher expression levels of foreign DNA genes. The genomes of these amplified recombinant host cells share features with the genomes of the high copy number recombinant host cells of this invention and with the genomes of high copy number transformants produced by classical gene amplification techniques, but are distinct from either. These recombinant host cells too are novel.

In order that this invention may be more fully understood, the following Examples are set forth. These Examples are for purposes of illustration only and this invention should not be construed to be limited by any recitation used therein.

EXAMPLE 1

Effect of Methotrexate Concentration During Secondary Selection on

DHFR⁻Gene Copy Number in CHO Cells

Cells and Media

DHFR⁻CHO cells were subcloned from the clone designated CHO-DUKX-B1 of Urlaub and Chasin, "Isolation of Chinese Hamster Cell Mutants Deficient in Dihydrofolate Reductase Activity", *Proc. Natl. Acad. Sci. USA*, 77, pp. 4216–20 (1980). This clone was kindly provided by Dr. P. A. Sharp (Massachusetts Institute of Technology, Boston, Mass.), who obtained the clone from Dr. L. Chasin (Columbia University, New York, N.Y.). The cells were grown in MEM alpha supplemented with ribonucleotides and deoxyribonucleotides (10 mg/L each of adenosine, cytidine, guanosine, uridine, 2'-deoxyadenosine, 2'-deoxyguanosine and 2'-deoxythymidine; 11 mg/L of 2'-deoxycytidine hydrochoride) (Gibco Laboratories, Grand Island, N.Y.), 10% fetal bovine serum (Hazleton, Lenexa, Kans.) and 4 mM glutamine (M.A. Bioproducts, Walkersville, Md.) ("α+medium").

For primary selection, DHFR−CHO cells were transferred to MEM alpha supplemented with 10% dialyzed fetal bovine serum (Hazleton) and 4 mM glutamine and lacking ribonucleotides and deoxyribonucleotides ("α−medium").

For secondary selection, the cells were cultured in α−medium supplemented with methotrexate ("α−/MTX medium") (Sigma Chemica Co., St. Louis, MO) (see Table I or II for the various MTX concentrations tested).

Expression Vectors

The vector pSV2-DHFR (FIG. 1) expresses DHFR from the SV40 early promoter. The construction of this vector is described in Subramani et al., "Expression of the Mouse Dihydrofolate Reductase Complementary Deoxyribonucleic acid in Simian Virus 40 Vectors", *Mol. Cell. Biol.*, 1(9), pp. 854–64 (1981). Vector pSV2-DHFR, harbored in *E. coli* strain HB101, is available from the American Type Culture Collection, Rockville, Md. (ATCC 37146).

Electroporation and Selection of High Copy Number CHO Cells

This example summarizes the results of two separate experiments (i.e., selection of high copy number cells from two independent electroporations). Both of these experiments were performed identically, and are described below. Unless otherwise noted, all operations were performed at room temperature.

Foreign DNA was prepared for transfer into host cells as follows. Two hundred micrograms of the vector pSV2-DHFR were digested overnight at 37° C. with EcoRI to linearize the DNA (400 μl reaction containing 200 μg DNA and 100 units EcoRI). After digestion, 200 μg of salmon sperm DNA, previously sonicated to 300–1000 bp size, were added to the linearized vector and the mixture of DNAs was precipitated. To precipitate, 5 M NaCl was added to a final concentration of 0.1 M. Next, 2.5 volumes of ethanol were added, and the mixture incubated for ten minutes on dry ice. After a ten minute centrifugation at 4° C. in an Eppendorf centrifuge (model 5414), the ethanol was aspirated and the DNA pellet was air-dried for 15 minutes in a tissue culture hood. Eight hundred microliters of 1X HeBS (20 mM Hepes/NaOH, pH 7.05; 137 mM NaCl; 5 mM KCl; 0.7 mM $Na_2HPO_4$; 6 mM dextrose) were added to the DNA pellet. The DNA was allowed to resuspend in the 1X HeBS for at least two hours prior to electroporation. Immediately prior to electroporation, the DNA was pipetted up and down several times to mix.

Each electroporation procedure utilized approximately $2 \times 10^7$ DHFR−CHO cells. These cells were fed or passaged on the day prior to electroporation and were approximately 50% confluent on 10 cm plates at the time of harvesting for electroporation. Cells were detached from the plates by trypsin treatment. The trypsin was subsequently inactivated by the addition of 8.0 ml α+ medium per plate. The contents of the plates were then centrifuged at 1000 rpm for 4 minutes in an IEC HN-SII table-top centrifuge ($\sim 200 \times g_{av}$) to pellet the cells. The medium was aspirated off of the cell pellet and the cells were resuspended in the remaining media by flicking the tube.

The plasmid and salmon sperm DNA (in 800 μl 1X HeBS) were added to the cell suspension and the mixture immediately transferred to an electroporation cuvette (Bio-Rad). The Bio-Rad Gene Pulser TM apparatus was used, with the capacitance set at 960 μFd and the voltage set at 300 V. To electroporate, one pulse was delivered to the contents of the cuvette at room temperature. No preincubation of the cell suspension/DNA mixture was required prior to the pulse. The duration of the pulse was approximately 10 milliseconds. The cells were incubated for 8–10 minutes at room temperature in the cuvette following electroporation and then were transferred to a 15-ml tube containing 14 ml of α+medium. The cells were then centrifuged as above. After aspirating the medium, the wet cell pellet was resuspended by flicking fresh α+medium was added and the cells were pipetted gently up and down once or twice to resuspend further. The cells were then seeded into 10 cm plates. Approximately 20–30% of the viable CHO cells are expected to incorporate foreign DNA and, thus, survive primary selection. Therefore, approximately $1 \times 10^7$ total cells per 10 cm plate were seeded. To allow the cells to recover from electroporation, the cells were initially seeded into α+non-selective medium.

Cells were cultured in a 37° C., 5.5% $CO_2$ incubator. After a recovery period of two days, the cells were removed from the culture plates by trypsin treatment, counted, and seeded into six 10 cm plates at a density of about $1 \times 10^6$ cells per plate, in α−medium. The cells were incubated for four days in this primary selection medium (α−medium). Approximately 15–30% of DHFR−CHO cells were stably transformed to α−resistance under these conditions, indicating that these cells had incorporated at least one copy of foreign DNA and were expressing the DHFR gene. After the four-day primary selection, the plates became nearly confluent with growing α−resistant cells (α−sensitive cells detach very slowly from the plates and after four days a large amount of sick, non-growing cells will remain attached).

After the four-day primary selection, the cells were subjected to secondary selection, to select for cells that had incorporated foreign DNA at a high copy number. The cells were again removed from the culture plates by trypsin treatment, counted, and seeded at a density of approximately $1 \times 10^6$ cells per plate into 10 cm plates containing α−/MTX medium (eight plates for each MTX concentration; see Tables I and II for the various MTX concentrations tested). After 6–7 days, the original medium was removed and the cells were fed with the fresh α−/MTX medium of the same composition. After 14 days of secondary selection, colonies ($\sim 1$ mm diameter) were picked using a pipetman and seeded at one colony per well into 48-well tissue culture dishes In both experiments A and B, ten clones were picked after secondary selection for analysis at each MTX concentration, with the exception that at 0.5 μM MTX, twenty clones were picked from experiment A and twenty five from experiment B.

At confluence, the cells were transferred to 6-well dishes and later to 10 cm tissue culture plates The cells were maintained in the same α−/MTX medium at all times.

The cells in 10 cm plates were fed with fresh α−/MTX medium at 50% confluence and were then detached by trypsin treatment One-half of the cells was frozen down (overnight at −80° C.) in 10% DMSO/90% α−medium and then stored in liquid nitrogen until use. The other half of the cells was used as a source of genomic DNA for later Southern blot analysis to determine copy number.

Determination of DHFR Gene Copy Number

Nucleic acid was harvested from confluent or near-confluent 10 cm plates by removal of the culture medium followed by addition of 0.5 ml of a buffer containing proteinase K at 200 µg/ml in 0.5% sodium dodecyl sulfate/20 mM Tris/HCl, pH 8/10 mM EDTA/10 mM sodium chloride. The resulting lysate was transferred to a 1.5 ml tube and incubated overnight at 37° C.

The nucleic acid was extracted twice with phenol, once with chloroform, and once with ether. Next, the nucleic acid was precipitated by the addition of sodium chloride to 0.1 M and 2.5 volumes of ethanol, followed by incubation for five minutes on dry ice. The nucleic acid was pelleted by a ten-minute centrifugation at 4° C. in an Eppendorf centrifuge (model 5414). The pellet was rinsed with −80° C. ethanol, and then dried under vacuum. The nucleic acid was resuspended in 50 µl double-distilled water. Absorbance readings at 260 nm indicated yields of 50–100 µg of nucleic acid per 10 cm plate.

For analysis, 20 µg of nucleic acid was digested to completion (at least six hours, and often overnight, at 37° C.) with PvuII and BglII. Digested DNA samples (20 µg nucleic acid per lane) were elecrophoresed on 8% agarose gels run in 1x TBE (see Maniatis et al., "Molecular Cloning: A Laboratory Manual", Cold Spring Harbor Laboratory, Cold Spring Harbor, N.Y. (1980)). Each gel also contained several lanes of plasmid standards. The standards consisted of digested (PvuII and BglII pSV2-DHFR corresponding to various DHFR copy numbers of between 1 and 1000 copies per cell (usually corresponding to 2, 10, 50, 250, and 1000 copies). Assuming values of $3 \times 10^9$ base pairs per genome and 10 µg DNA per 20 µg nucleic acid (amount loaded per lane), we computed the amount of digested plasmid required to give a single copy hybridization signal as being 16 pg pSV2-DHFR. This number was confirmed by comparison with hybridization signals of genomic DNA from clones known to contain only a single copy of pSV2-DHFR.

After electrophoresis, the nucleic acid in the agarose gels was transferred to Gene Screen ™ hybridization membranes, using the protocol set forth in the Gene Screen ™ manual (New England Nuclear, Boston, MA, #NEF-972). Pre-hybridization, hybridization, and washes were also performed according to the Gene Screen ™ protocol.

The hybridization probe used was the $^{32}$P-labelled 1000 bp PvuII/BglII fragment of pSV2-DHFR. The gel-purified fragment was labelled with $^{32}$P according to the method of Feinberg and Vogelstein, "A Technique for Radiolabelling DNA Restriction Endonuclease Fragments to High Specific Activity", Anal. Biochem., 137, pp. 266–67 (1984).

After hybridization and washing (see above), the membranes were exposed to x-ray film at −80° C. Several films, exposed for differing times, were taken of each membrane. Copy number was then determined by comparing the intensities of bands in the genomic DNA lanes with the same bands in the lanes containing the digested plasmid standards.

TABLE I

Effect of MTX Concentration on Frequency of Resistant Colonies

| [MTX] µM | Frequency of Resistant Colonies | |
|---|---|---|
| | A | B |
| 0.1 | $7.5 \times 10^{-5}$ | $1.2 \times 10^{-4}$ |
| 0.2 | $1.9 \times 10^{-5}$ | $3.5 \times 10^{-5}$ |
| 0.3 | $1.1 \times 10^{-5}$ | $1.5 \times 10^{-5}$ |
| 0.4 | $6.3 \times 10^{-6}$ | $8.2 \times 10^{-6}$ |
| 0.5 | $4.1 \times 10^{-6}$ | $5.0 \times 10^{-6}$ |
| 1.0 | $2.2 \times 10^{-6}$ | $1.6 \times 10^{-6}$ |

TABLE II

Effect of MTX Concentration on DHFR Gene Copy Number*

| [MTX] µM | Average Copy Number | | Copy Number Range | |
|---|---|---|---|---|
| | A | B | A | B |
| 0.1 | 8 | 6 | 4–20 | 2–14 |
| 0.2 | 14 | 17 | 8–25 | 10–25 |
| 0.3 | 31 | 18 | 15–40 | 4–25 |
| 0.4 | 41 | 60 | 8–120 | 6–250 |
| 0.5 | 113 | 109 | 15–500 | 10–800 |
| 1.0 | 106 | 92 | 20–400 | 25–300 |

*Ten clones were analyzed for copy number from each experiment at MTX concentrations of 0.1, 0.2, 0.3, 0.4 and 1.0 µM. At 0.5 µM MTX, 20 clones from experiment A and 25 clones from experiment B were analyzed.

EXAMPLE 2

Production of CHO Cells Containing the MIS Gene Integrated at High Copy Number

Cells and Media

The DHFR−CHO cells described in Example 1 were also used for this example. The non-selective and primary selection media are the same as that described in Example 1. However, for secondary selection, all cells were cultured in α−medium supplemented with 0.5 µM MTX.

Expression Vectors

The vector pJOD-10 (FIG. 2) contains, as product gene, the human Müllerian inhibiting substance ("MIS") gene. The MIS gene is expressed from the Adenovirus 2 major late promoter ("AdMLP"), along with the SV40 enhancer. The MIS gene was derived from both cDNA and genomic DNA clones. Downstream from the MIS poly A addition site and 3'-genomic flanking sequence are SV40 splice and polyadenylation sites. This vector also contains the murine DHFR gene, derived from cDNA. The DHFR gene is expressed from the SV40 early promoter and is followed by SV40 splice and polyadenylation signals. The DHFR and MIS genes are expressed in opposite orientations. Between the two SV40 poly A sites is a transcriptional termination element. This element was synthesized as an oligonucleotide homologous to the human gastrin gene transcriptional termination sequence (see Sato et al., supra). This terminator element is employed in order to block transcriptional interference between the MIS and DHFR genes. The pJOD-10 vector also contains the ampicillin-resistance gene and the ColE1 bacteria origin of replication derived from pBR327, allowing cloning and amplification of this vector in bacteria.

Vector pJOD-10 was constructed (see FIG. 2) from DNA of three origins: (1) vector pD1 (which comprises the human MIS gene); (2) vector pSV2-DHFR (which comprises the murine DHFR gene); and (3) synthetic oligonucleotide homologous to the human gastrin gene transcriptional terminator. The construction of pD1 is described in Cate et al., European patent application 221,761. The construction of vector pSV2-DHFR is described in Subramani et al., supra and is available from the American Type Culture Collection (ATCC 37146).

Two complementary oligonucleotides homologous to the human gastrin transcriptional terminator were synthesized according to standard procedures using an Applied Biosystems 380A DNA Synthesizer. These oligonucleotides were isolated by gel chromatography. The oligonucleotide corresponding to the gastrin gene coding strand is 51 nucleotides long and comprises a sequence homologous to nucleotides +190 to +233 of the human gastrin gene, according to the map coordinates and sequence of Sato et al., supra. The complementary oligonucleotide is 59 nucleotides long. These oligonucleotides were annealed, forming a double stranded DNA molecule ("term") with an ApaI overhang at one end and an XhoI site and EcoRI overhang at the other end:

and were evaluated for MIS gene copy number and for MIS production level.

Determination of MIS Production Levels

MIS production levels were determined using the following sandwich ELISA protocol. Except where otherwise indicated, solutions added in washing steps filled the wells and other reagent solutions were added to the microtiter plate wells at a volume of 50 μl well. Except where otherwise indicated, all incubations were performed at room temperature.

A solution containing monoclonal anti-MIS antibody M10.6 at a concentration of 25 μg/ml in 0.05 M sodium carbonate/bicarbonate buffer, pH 9.6 was added to each well of 96-well Dynatech Immulon II microtiter plates. The plates were then covered with Parafilm and incubated overnight to coat the wells. The next day, the contents of the plates were removed by shaking, and the plates were washed six times with water. Next, 150 μl of block buffer (5% fetal calf serum in phosphate buffered saline, filtered through 2 μm filter) were added to each well, and the plates were incubated for two hours.

```
        +190                                              +233
         |                                                 |
5'      CCTTTTTTTTTAATTTTTATTTTTATTTTTATTTTTGAGATGGAGTCTCGAGG            3'
3' CCGGGGAAAAAAAAATTAAAAATAAAATAAAATAAAAACTCTACCTCAGAGCTCCTTAA 5'
```

Vector pSV2-DHFR was cut with EcoRI and ApaI and the large fragment was gel purified. The double stranded term insert was then ligated into the ApaI/EcoRI pSV2-DHFR fragment, forming vector pDT4. Vector pDT4 was cut with AatII and XhoI and the large fragment was ge purified. Vector pD1 was cut with SalI and AatII and the large fragment was gel purified. The SalI/AatII pD1 large fragment was inserted into the AatII/XhoI pDT4 large fragment, forming pJOD-10.

Vector pJOD-10, harbored in *E. coli* strain MC1061 was deposited in the In Vitro International, Inc. culture collection, in Linthicum, Maryland, on April 22, 1988. It is identified as "pJOD-10" and has been assigned accession number IVI-10167.

Electroporation and Selection of High Copy Number CHO Cells

The protocol for production of CHO cells containing foreign DNA (pJOD-10) integrated at high copy number was the same as that followed in Example 1 except for the changes noted below.

Approximately $2 \times 10^7$ DHFR$^-$ CHO cells were electroporated as described in Example 1 with a mixture consisting of 200 μg vector pJOD-10 and 200 μg sonicated salmon sperm DNA (as carrier). Vector pJOD-10 was linearized prior to electroporation by digestion overnight at 37° C. with AatII. After a two-day recovery period in $\alpha^+$(non-selective) medium, the cells were seeded into $\alpha^-$(primary selection) medium. The cells were cultured in this primary selection medium for four days. As in Example 1, approximately 15–30% of DHFR- CHO cells survived primary selection. Cells surviving primary selection were seeded into $\alpha^-$ medium supplemented with 0.5 μM MTX (the secondary selection medium). After 14 to 16 days of secondary selection, approximately fifty colonies remained, corresponding to a survival frequency of $4.2 \times 10^{-6}$. Twelve of these colonies were picked and expanded, preparatory to analysis. All twelve colonies survived expansion and were evaluated for MIS gene copy number and for MIS production level.

After shaking out the blocking buffer, conditioned media (containing MIS), and several dilutions of conditioned media in block buffer, were added to the plates. Each plate included a row of dilutions of a solution containing pure MIS of known concentration (for standard curve) in block buffer, as well as a row of dilutions of block buffer alone (negative control). The plates were incubated for one hour.

The contents of the plates were then shaken out and the plates washed six times with water. Rabbit polyclonal anti-MIS Ab 848, at 1:1000 dilution in block buffer, was added to every well and the plates were incubated for one hour.

After shaking out the contents of the plate, the wells were washed four times with wash buffer (0.05% Tween 20 in phosphate buffered saline). Horseradish peroxidase-conjugated goat anti-rabbit IgG (H+L) (Kirkegaard & Perry Laboratories, Inc., Gaitherburg, Md., #041506), at 1:500 dilution in block buffer supplemented with 1% whole mouse serum (Cooper Biomedical, Inc., Malvern, Penna., #5011-1380), was added to every well. The plates were incubated at 4° C. for 50–60 minutes. After this incubation, the contents of the plates were shaken out and the plates were washed six times with wash buffer.

TMB/substrate buffer was added to every well and the development of blue color was monitored at 650 nm in a microtiter plate reader. After 10-15 minutes, color development was stopped by the addition to every well of 50 μl 2 N sulfuric acid. This addition changes the color of the solution from blue to yellow. Finally, after manually blanking the machine on one of the wells in the negative control row, the plate was automatically read at 450 nm.

TMB/substrate buffer was prepared immediately before use as follows: One milliliter of 42 mM tetramethylbenzidine (ICN Immunobiologicals, Lisle, Ill., #980501) in dimethylsulfoxide (Aldrich) was added dropwise to 100 ml of room temperature 0.1 M sodium acetate/citric acid, pH 4.9. Lastly, 14.7 μl 30% hydrogen peroxide (Sigma Chemical Co. #H-1009) were added.

Determination of MIS Gene Copy Number

The MIS gene copy number of the twelve clones was determined analogously to the procedure followed in Example 1 for DHFR copy number, with the following modifications. In preparation for electrophoresis, nucleic acid isolated from the cells of this example was digested to completion with PvuII. For the plasmid standard lanes, pJOD-10 was likewise digested with PvuII. With respect to the plasmid standard lanes, the amount of digested pJOD-10 required to give a single copy hybridization signal was computed to be 33 pg. Finally, the hybridization probe in this example was the $^{32}$P-labelled 1964 bp PvuII DNA fragment of pJOD-10 (pJOD-10 map coordinates 1854 to 3818).

TABLE III
HIGH COPY NUMBER ELECTROPORATION OF CHO CELLS WITH pJOD-10

| Clone | MIS production (pg/cell/day) | MIS gene copy number (copies per cell) |
|---|---|---|
| 1 | 1.7 | 140 |
| 2 | 1.2 | 110 |
| 3 | 0.7 | 25 |
| 4 | 1.1 | 60 |
| 5 | 3.5 | 400 |
| 6 | <0.1 | 10 |
| 7 | 0.8 | 50 |
| 8 | 0.5 | 100 |
| 9 | 6.0 | 700 |
| 10 | 0.3 | 40 |
| 11 | <0.1 | 10 |
| 12 | 3.6 | 250 |

Table III displays the MIS gene copy number and the MIS production levels of the twelve clones picked for analysis. This data demonstrates that the process of this invention produces cells containing stably integrated foreign DNA at high copy number. The level of MIS production of al twelve clones was directly proportional to their MIS gene copy number. Eight of the twelve cones isolated have a high MIS gene copy number (over 50 copies/cell).

EXAMPLE 3
Production of 3T3 Cells Containing the MIS Gene Integrated at High Copy Number

Cells and Media

NIH/3T3 cells (ATCC CRL 1658) were propagated in DMEM (Gibco Laboratories) supplemented with ("DC medium"). For primary selection, the cells were cultured in DC medium, further supplemented with G418 (Gibco Laboratories) at 0.7 mg/ml ("DC-G medium"). For secondary selection, the cells were cultured in DC medium supplemented with 0.5 μM MTX ("DC/MT medium").

Expression Vectors

Figure 3:
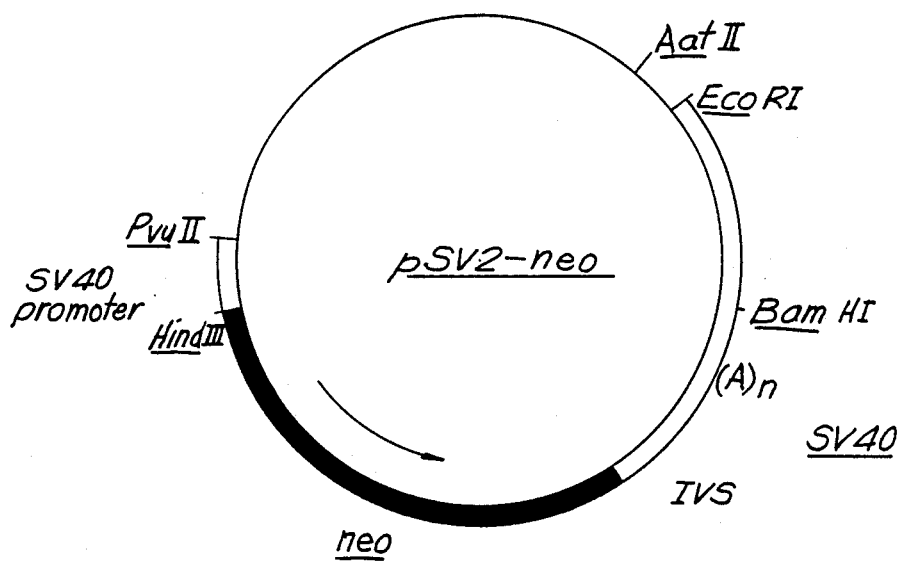
FIG. 3 is a pictorial representation of vector pSV2-neo.
Figure 2:
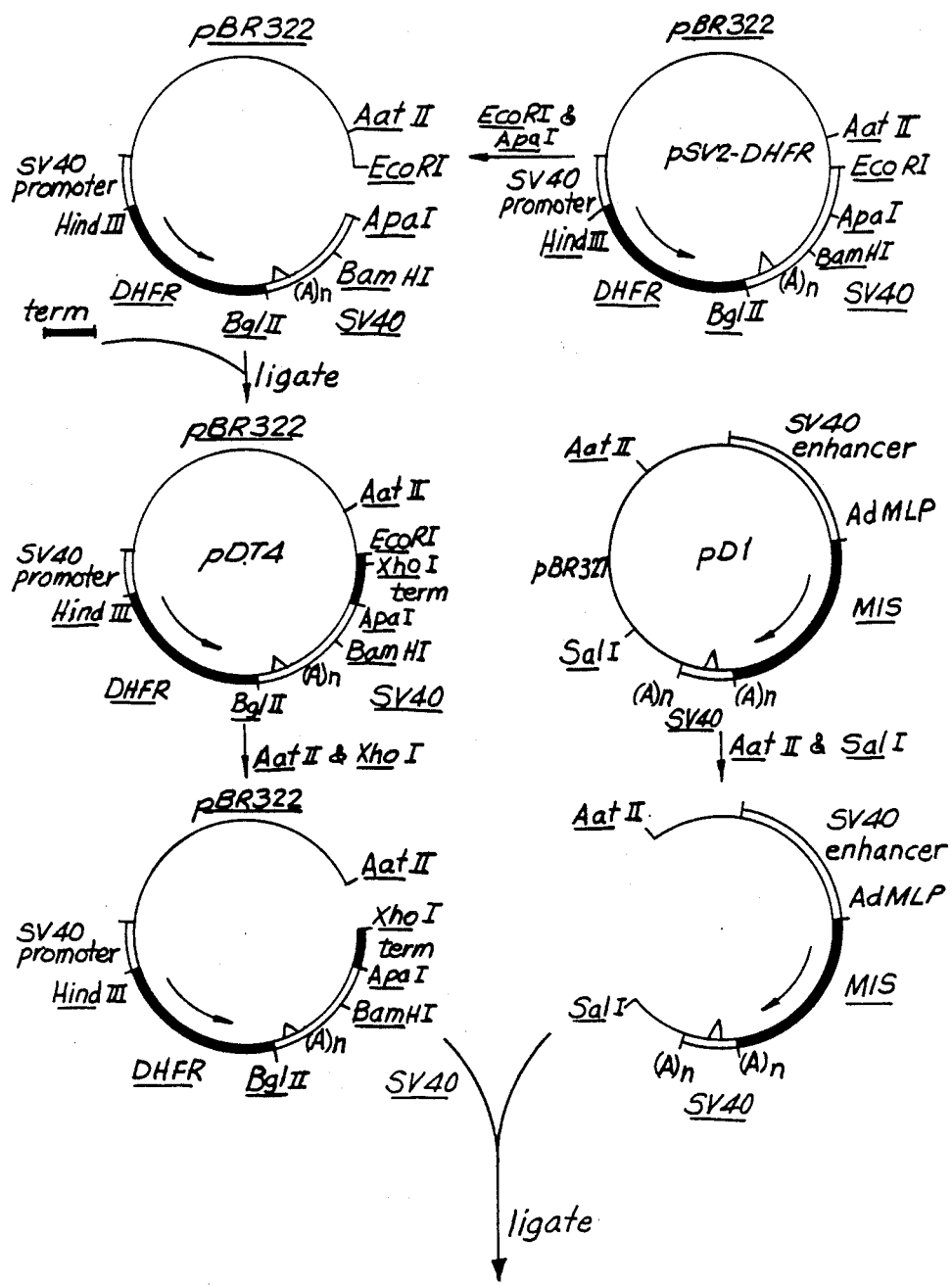
FIG. 2 is a pictorial representation of the construction of vector pJOD-10.

Protective (DHFR) and product (MIS) genes were supplied by vector pJOD-10 (see FIG. 2). Vector pJOD-10 is described in Example 2. Vector pSV2-neo (FIG. 3) contains the bacterial neo gene, which codes for G418-resistance in mammalian cells. The construction of pSV2-neo is described in Southern and Berg, "Transformation of Mammalian Cells to Antibiotic Resistance with a Bacterial Gene under Control of the SV40 Early Region Promoter", *J. Mol. Appl. Genet.*, 1, pp. 327–41 (1982). The neo gene functions as a selective gene. In pSV2-neo, the neo gene is expressed from the SV40 early promotor. Vector pSV2-neo, harbored in *E. coli* strain HB101, is available from the American Type Culture Collection (ATCC 37149).

Electroporation and Selection of High Copy Number 3T3 Cells

The protocol for production of NIH/3T3 cells (a DHFR+cell line) with high copy number integrated foreign DNA was the same as that followed in Example 1 for DHFR−CHO cells except for the changes noted below.

Approximately $2 \times 10^7$ 3T3 cells were electroporated with a DNA mixture consisting of 220 μg pJOD-10, 40 μg pSV2-neo and 140 μg sonicated salmon sperm carrier DNA. Both the pJOD-10 and pSV2-neo vectors were digested overnight at 37° C. with AatII to linearize them prior to electroporation. Electroporation was performed in a Bio-Rad Gene Pulser ™ by use of one pulse at 960 μFd and 270 V. After a 2-day recovery period in non-selective medium (DC medium), the cells were seeded at $6 \times 10^5$ cells per 10 cm plate into primary selection medium (DC-G medium). The primary selection step consisted of G418 selection for expression of the neo gene. The primary selection lasted 5 days, at the end of which approximately 5% of the 3T3 cells survived G418 selection. These cells were seeded, at $8 \times 10^5$ cells per 10 cm plate, into DC/MTX medium. After 14 days of secondary selection, eleven colonies remained, corresponding to a secondary selection survival frequency of $8.5 \times 10^{-7}$. These colonies were picked and expanded as described in Example 1. Three colonies did not survive expansion. The MIS production level and the MIS gene copy number of the eight remaining colonies were determined as described in Example 2, and are displayed in Table IV.

TABLE IV
HIGH COPY NUMBER ELECTROPORATION OF 3T3 CELLS

| Clone | MIS production (pg/cell/day) | MIS gene copy number (copies per cell) |
|---|---|---|
| 1 | 1.3 | 120 |
| 2 | 1.9 | 80 |
| 3 | 0.6 | 20 |
| 4 | 3.7 | 200 |
| 5 | 0.8 | 15 |
| 6 | 2.5 | 150 |
| 7 | 0.2 | 10 |
| 8 | 1.2 | 50 |

We claim:
1. A method for preparing recombinant host cells containing foreign DNA at a copy number of 50 or greater, said method comprising the following steps:
   (a) subjecting a population of cells to electroporation in the presence of said foreign DNA, wherein said foreign DNA comprises:
      (i) at least one protective gene coding for a protein capable of protecting said recombinant host cells against a toxic substance, wherein increasingly higher copy numbers of said protective gene are required for, and capable of, protecting said recombinant host cell against increasing concentrations of said toxic substance,
      (ii) at least one product gene coding for a polypeptide whose production is desired, said genes being operably linked to regulatory sequences that are compatible with said recombinant host cells;

(b) culturing the cells produced in step (a) for a time sufficient to allow these cells to recover from the electroporation process;

(c) exposing the cells produced in step (b) to a sufficient concentration of said toxic substance to kill or severely retard the division of those cells with a copy number of less than 50.

2. A method for preparing recombinant host cells containing foreign DNA at a copy number of 50 or greater, said method comprising the following steps:

(a) subjecting a population of cells to electroporation in the presence of said foreign DNA, wherein said foreign DNA comprises:
 (i) at least one protective gene coding for a protein capable of protecting said recombinant host cells against a toxic substance, where increasingly higher copy numbers of said protective gene are required for, and capable of, protecting said recombinant host cells against increasing concentrations of said toxic substance,
 (ii) at least one product gene coding for a polypeptide whose production is desired,
 (iii) at least one selective gene coding for a protein, wherein the presence of one copy per cell of said selective gene is sufficient to protect said recombinant host cells against either a decreased concentration of a nutritive substance or the presence of a toxic substance,
said genes being operably linked to regulatory sequences that are compatible with said recombinant host cells;

(b) culturing the cells produced in step (a) for a time sufficient to alow these cells to recover from the electroporation process;

(c) exposing the cells produced in step (b) to either:
 (i) a toxic substance against which the product of said selective gene provides protection, at a concentration sufficient to kill or severely retard the division of those cells which did not incorporate at least one copy of foreign DNA in the electroporation process of step (a), or
 (ii) a decreased amount of the nutritive substance which the product of said selective gene makes non-essential at a concentration sufficient to kill or severely retard the division of those cells which did not incorporate at least one copy of foreign DNA in the electroporation process of step (a);

(d) exposing the cells produced in step (c) to a toxic substance at a concentration sufficient to kill or severely retard the division of those cells with a copy number of less than 50, wherein said toxic substance is the substance against which the product of said protective gene provides protection.

3. A method for preparing recombinant host cells containing foreign DNA at a copy number of 50 or greater, said method comprising the following steps:

(a) subjecting an initial population of cells to electroporation in the presence of said foreign DNA, wherein said foreign DNA comprises:
 (i) at least one protective gene coding for a protein capable of protecting said recombinant host cells against decreases in the concentration of a nutritive substance that is essential in the absence of said protective gene, wherein increasingly higher copy numbers of said protective gene are required for, and capable of, protecting said recombinant host cells against decreasing concentrations of said nutritive substance,
 (ii) at east one product gene coding for a polypeptide whose expression is desired,
said genes being operably linked to regulatory sequences which are compatible with said recombinant host cells;

(b) culturing the cells produced in step (a) for a time sufficient to allow these cells to recover from the electroporation process;

(c) exposing cells produced in step (b) to a sufficient concentration of said nutritive substance to kill o severely retard the division of those cells with a copy number of less than 50.

4. A method for preparing recombinant host cells containing foreign DNA at a copy number of 50 or greater, said method comprising the following steps:

(a) subjecting a population of cells to electroporation in the presence of said foreign DNA, wherein said foreign DNA comprises:
 (i) at least one protective gene coding for a protein capable of protecting said recombinant host cells against decreases in the concentration of a nutritive substance that is essential in the absence of said protective gene, wherein increasingly higher copy numbers of said protective gene are required for, and capable of, protecting said recombinant host cells against decreasing concentrations of said nutritive substance,
 (ii) at least one product gene coding for a polypeptide whose production is desired,
 (iii) at least one selective gene coding for a protein, wherein the presence of one copy per cell of said selective gene is sufficient to protect said recombinant host cells from either a decreased concentration of a nutritive substance or the presence of a toxic substance,
said genes being operably inked to regulatory sequences which are compatible with said recombinant host cells:

(b) culturing the cells produced in step (a) for a time sufficient to allow these cells to recover from the electroporation process;

(c) exposing the cells produced in step (b) to either:
 (i) a toxic substance against which the product of said selective gene provides protection, at a concentration sufficient to kill or severely retard the division of those cells which did not incorporate at least one copy of foreign DNA in the electroporation process of step (a), or
 (ii) a decreased amount of the nutritive substance which the product of said selective gene makes non-essential, at a concentration sufficient to kill or severely retard the division of those cells which did not incorporate at least one copy of foreign DNA in the electroporation process of step (a);

(d) exposing the cells produced in step (c) to a nutritive substance, at a concentration sufficient to kill or severely retard the division of those cells with a copy number of less than 50, wherein said nutritive substance is the substance which the product of said protective gene makes non-essential.

5. A method for improving production of a desired gene product in recombinant host cells containing a DNA sequence coding for that product, said method comprising the following steps:
  (a) subjecting a population of cells to electroporation in the presence of foreign DNA, wherein said foreign DNA comprises:
    (i) at least one protective gene coding for a protein capable of protecting said recombinant host cell against a toxic substance, wherein increasingly higher copy numbers of said protective gene are required for, and capable of, protecting said recombinant host cell against increasing concentrations of said toxic substance,
    (ii) at least one product gene coding for a polypeptide whose production is desired,
  said genes being operably linked to regulatory sequences which are compatible with said recombinant host cells;
  (b) culturing the cells produced in step (a) for a time sufficient to allow these cells to recover from the electroporation process;
  (c) exposing the cells produced in step (b) to a sufficient concentration of said toxic substance to kill or severely retard the division of those cells with a copy number of less than 50;
  (d) culturing the cells produced in step (c).

6. A method for improving production of a desired gene product in recombinant host cells containing a DNA sequence coding for that product, said method comprising the following steps:
  (a) subjecting a population of cells to electroporation in the presence of foreign DNA, wherein said foreign DNA comprises:
    (i) at least one protective gene coding for a protein capable of protecting said recombinant host cells against a toxic substance, where increasingly higher copy numbers of said protective gene are required for, and capable of, protecting said recombinant host cells against increasing concentrations of said toxic substance,
    (ii) at least one product gene coding for a polypeptide whose production is desired,
    (iii) at least one selective gene coding for a protein, wherein the presence of one copy per cell of said selective gene is sufficient to protect said recombinant host cells from either a decreased concentration of a nutritive substance or the presence of a toxic substance,
  said genes being operably linked to regulatory sequences compatible with said recombinant host cells;
  (b) culturing the cells produced in step (a) for a time sufficient to allow these cells to recover from the electroporation process;
  (c) exposing the cells produced in step (b) to either;
    (i) a toxic substance against which the product of said selective gene provides protection, at a concentration sufficient to kill or severely retard the division of those cells which did not incorporate at least one copy of foreign DNA in the electroporation process of step (a), or
    (ii) a decreased amount of the nutritive substance which the product of said selective gene makes non-essential, at a concentration sufficient to kill or severely retard the division of those cells which did not incorporate at least one copy of foreign DNA in the electroporation process of step (a);
  (d) exposing the cells produced step (c) to a toxic substance at a concentration sufficient to kill or severely retard the division of those cells with a copy number of less than 50, wherein said toxic substance is the substance against which the product of said protective gene provides protection;
  (e) culturing the cells produced in step (d).

7. A method for improving production of a desired gene product in recombinant host cells containing a DNA sequence coding for that product, said method comprising the following steps:
  (a) subjecting a population of cells to electroporation in the presence of foreign DNA, wherein said foreign DNA comprises:
    (i) at least one protective gene coding for a protein capable of protecting said recombinant host cell against decreases in the concentration of a nutritive substance that is essential in the absence of said protective gene, wherein increasingly higher copy numbers of said protective gene are required for, and capable of, protecting said recombinant host cells against decreasing concentrations of said nutritive substance,
    (ii) at least one product gene coding for a polypeptide whose expression is desired,
  said genes being operably linked to regulatory sequences which are compatible with said recombinant host cells;
  (b) culturing the cells produced in step (a) for a time sufficient to alow these cells to recover from the electroporation process;
  (c) exposing cells produced in step (b) to a sufficient concentration of said nutritive substance to kill or severely retard the division of those cells with a copy number of less than 50;
  (d) culturing the cells produced in step (c).

8. A method for improving production of a desired gene product in recombinant host cells containing a DNA sequence coding for that product, said method comprising the following steps:
  (a) subjecting a population of cells to electroporation in the presence of foreign DNA, wherein said foreign DNA comprises:
    (i) at least one protective gene coding for a protein capable of protecting said recombinant host cells against decreases in the concentration of a nutritive substance that is essential in the absence of said protective gene, wherein increasingly higher copy numbers of said protective gene are required for, and capable of, protecting said recombinant host cells against decreasing concentrations of said nutritive substance,
    (ii) at least one product gene coding for a polypeptide whose production is desired,
    (iii) at least one selective gene coding for a protein, wherein the presence of one copy per cell of said selective gene is sufficient to protect said recombinant host cells from either a decreased concentration of a nutritive substance or the presence of a toxic substance,
  said genes being operably linked to regulatory sequences which are compatible with said recombinant host cells;
  (b) culturing the cells produced in step (a) for a time sufficient to allow these cells to recover from the electroporation process;
  (c) exposing the cells produced in step (b) to either:

(i) a toxic substance against which the product of said selective gene provides protection, at a concentration sufficient to kill or severely retard the division of those cells which did not incorporate at least one copy of foreign DNA in the electroporation process of step (a), or (ii) a decreased amount of the nutritive substance which the product of said selective gene makes non-essential, at a concentration sufficient to kill or severely retard the division of those cells which did not incorporate at least one copy of foreign DNA in the electroporation process of step (a);

(d) exposing the cells produced in step (c) to a nutritive substance at a concentration sufficient to kill or severely retard the division of those cells with a copy number of less than 50, wherein said nutritive substance is the substance which the product of said protective gene makes non-essential;

(e) culturing the cells produced in step (d).

9. Recombinant host cells or host cell cultures containing integrated foreign DNA at a copy number of 50 or greater, prepared according to the methods of any one of claims 1 to 4.

10. Recombinant host cells or host cell cultures, wherein the genomes of said recombinant host cells comprise foreign DNA, and wherein said foreign DNA is inserted into the genomes of said recombinant host cells at a copy number of 50 or greater in the form of tandem or inverted tandem repeats, with each repeating unit containing only foreign DNA, and wherein said foreign DNA comprises:

(a) a product gene coding for a protein whose expression is desired, (b) a protective gene coding for a protein capable of protecting said recombinant host cells from either the presence of a toxic substance or the absence of a nutritive substance, wherein increasingly higher copy numbers of said protective gene are required to protect said recombinant cells against, respectively, increasing concentrations of said toxic substance or decreasing concentrations of said nutritive substance, said genes being operably linked to regulatory sequences which are compatible with said recombinant host cells.

11. Recombinant host cells or host cell cultures, wherein the genomes of said recombinant host cells comprise foreign DNA, and wherein said foreign DNA is inserted into the genomes of said recombinant host cells at a copy number of 50 or greater in the form of tandem or inverted tandem repeats, with each repeating unit containing only foreign DNA, and wherein said foreign DNA comprises:

(a) a product gene coding for a protein whose expression is desired, (b) a protective gene coding for a protein capable of protecting said recombinant host cells from either the presence of a toxic substance or the absence of a nutritive substance, wherein increasingly higher copy numbers of said protective gene are required to protect said recombinant cells against, respectively, increasing concentrations of said toxic substance or decreasing concentrations of said nutritive substance, (c) a selective gene coding for a protein, wherein the presence of one copy per cell of said selective gene is sufficient to protect said recombinant host cells from either the decreased concentration of a nutritive substance or the presence of a toxic substance, said genes being operably linked to regulatory sequences which are compatible with said recombinant host cells.

12. A method for improving production of a protein coded for by a product gene, comprising the step of culturing a recombinant host cell of claim 10 or 11.

13. The method according to any one of claims 1 to 8 or 12, wherein said protective gene is selected from the group of genes coding for a member of the group consisting of dihydrofolate reductase, metallothionein, CAD, 3-hydroxy-3-methylglutaryl coenzyme A reductase, uridine monophosphate synthetase, adenosine deaminase, glutamine synthetase, asparagine synthetase, ribonucleotide reductase, thymidilate synthetase, ornithine decarboxylase, and promoter glutathione S-transferase Ya.

14. The method according to claim 13, wherein said protective gene codes for dihydrofolate reductase.

15. The method according to any one of claims 1 to 8 or 12, wherein two or more of said genes of said foreign DNA are contained within a single DNA molecule.

16. The method according to any one of claims 1 to 8 or 12, wherein said foreign DNA is in the form of linear DNA molecules.

17. The method according to claim 16, wherein said linear DNA molecules have compatible cohesive ends.

18. The method according to claim 15, wherein said DNA molecule further comprises at least one eukaryotic transcriptional terminator sequence located downstream of at least one of said genes.

19. The method according to any one of claims 1 to 8 or 12, comprising the further step of culturing the cells produced in the final step in the presence of increasing amounts of the substance which said protective gene was designed to protect against, for a time sufficient to permit said cells to amplify said foreign DNA, said substance being present at a concentration sufficient to select those cells which have amplified said foreign DNA.

20. Recombinant host cells produced according to the method of claim 19.

* * * * *

UNITED STATES PATENT AND TRADEMARK OFFICE
CERTIFICATE OF CORRECTION

PATENT NO. : 4,956,288

DATED : September 11, 1990        Page 1 of 2

INVENTOR(S) : James G. Barsoum

It is certified that error appears in the above-identified patent and that said Letters Patent is hereby corrected as shown below:

Column 19, line 43, after "IVI-10167.", insert -- This deposit was transferred to the American Type Culture Collection, Rockville, Maryland, on June 20, 1991, where it is now available under accession number ATCC 68815. --.

Claim 2, column 23, line 36, "alow" should be -- allow --;

line 47, "non-essential" should be -- non-essential, --.

Claim 3, column 23, line 61, "an initial" should be -- a --;

column 24, line 14, "o" should be -- or --.

Claim 4, column 24, line 41, "inked" should be -- linked --;

line 43, "cells:" should be -- cells; --.

UNITED STATES PATENT AND TRADEMARK OFFICE
CERTIFICATE OF CORRECTION

PATENT NO. : 4,956,288
DATED : September 11, 1990
INVENTOR(S) : James G. Barsoum Page 2 of 2

It is certified that error appears in the above-identified patent and that said Letters Patent is hereby corrected as shown below:

Claim 6, column 25, line 55, "either;" should be -- either: --.

column 26, line 1, "produced step (c)" should be -- produced in step (c) --.

Claim 20, column 28, line 54, "Lo" should be -- to --.

Signed and Sealed this

Thirtieth Day of March, 1993

Attest:

STEPHEN G. KUNIN

*Attesting Officer*      *Acting Commissioner of Patents and Trademarks*